United States Patent [19]

Newman

[11] Patent Number: 5,301,686
[45] Date of Patent: Apr. 12, 1994

[54] FLUID SAMPLING METHOD

[75] Inventor: David P. Newman, Arvada, Colo.

[73] Assignee: COBE Laboratories, Inc., Lakewood, Colo.

[21] Appl. No.: 938,407

[22] Filed: Aug. 31, 1992

Related U.S. Application Data

[63] Continuation-in-part of Ser. No. 694,546, May 2, 1991, Pat. No. 5,167,238.

[51] Int. Cl.⁵ .............................................. A61B 5/00
[52] U.S. Cl. ................................... 128/760; 604/181; 604/236
[58] Field of Search ..................... 128/760, 763–766, 128/770; 604/52, 181, 182, 229, 233, 236, 240, 246, 249

[56] References Cited

U.S. PATENT DOCUMENTS

| | | |
|---|---|---|
| 2,844,964 | 7/1958 | Guilbert . |
| 3,143,109 | 8/1964 | Gewertz . |
| 3,459,177 | 8/1969 | Deuschle . |
| 3,557,778 | 1/1971 | Hughes . |
| 3,570,484 | 3/1971 | Steer . |
| 3,930,413 | 1/1976 | Laird et al. ............ 73/421 B |
| 3,957,052 | 5/1976 | Topham . |
| 4,108,173 | 8/1978 | Slivenko et al. . |
| 4,143,853 | 3/1979 | Abramson ............ 251/149.1 |
| 4,186,752 | 2/1980 | Guerra ................ 128/766 |
| 4,269,064 | 5/1981 | Johnson et al. ........ 73/422 TC |
| 4,324,239 | 4/1982 | Gordon et al. . |
| 4,387,879 | 6/1983 | Tauschinski ........... 604/247 |
| 4,484,912 | 11/1984 | Raible ................. 604/175 |
| 4,543,094 | 9/1985 | Barnwell .............. 604/236 |
| 4,580,452 | 4/1986 | Masson ............... 73/863.86 |
| 4,673,386 | 6/1987 | Gordon ................ 604/48 |
| 4,678,107 | 7/1987 | Ennis, III ............. 604/228 |
| 4,736,636 | 4/1988 | Fini et al. ............. 73/863.73 |
| 4,763,648 | 8/1988 | Wyatt ................. 128/673 |
| 4,917,491 | 4/1990 | Ring et al. ............ 356/300 |
| 5,114,400 | 5/1992 | Lynn ................... 604/53 |

FOREIGN PATENT DOCUMENTS

| | | |
|---|---|---|
| 0080379 | 1/1983 | European Pat. Off. . |
| 0293506 | 7/1988 | European Pat. Off. . |
| 858037 | 12/1952 | Fed. Rep. of Germany . |
| 75831 | 5/1970 | Fed. Rep. of Germany . |
| 2458545 | 6/1976 | Fed. Rep. of Germany . |
| 2815449 | 10/1978 | Fed. Rep. of Germany . |
| 3152062 | 9/1982 | Fed. Rep. of Germany . |
| 3546354 | 7/1987 | Fed. Rep. of Germany . |
| 2604237 | 3/1988 | France . |
| 9001352 | 2/1990 | PCT Int'l Appl. . |
| 2086349 | 5/1982 | United Kingdom . |

*Primary Examiner*—Max Hindenburg
*Attorney, Agent, or Firm*—William W. Rymer; Bruce R. Winsor

[57] ABSTRACT

A fluid sampling method in which a variable volume chamber between a needle site and a syringe creates a negative pressure at the tip on its removal from the needle site to reduce the exposure to liquid at the time of removal.

10 Claims, 1 Drawing Sheet

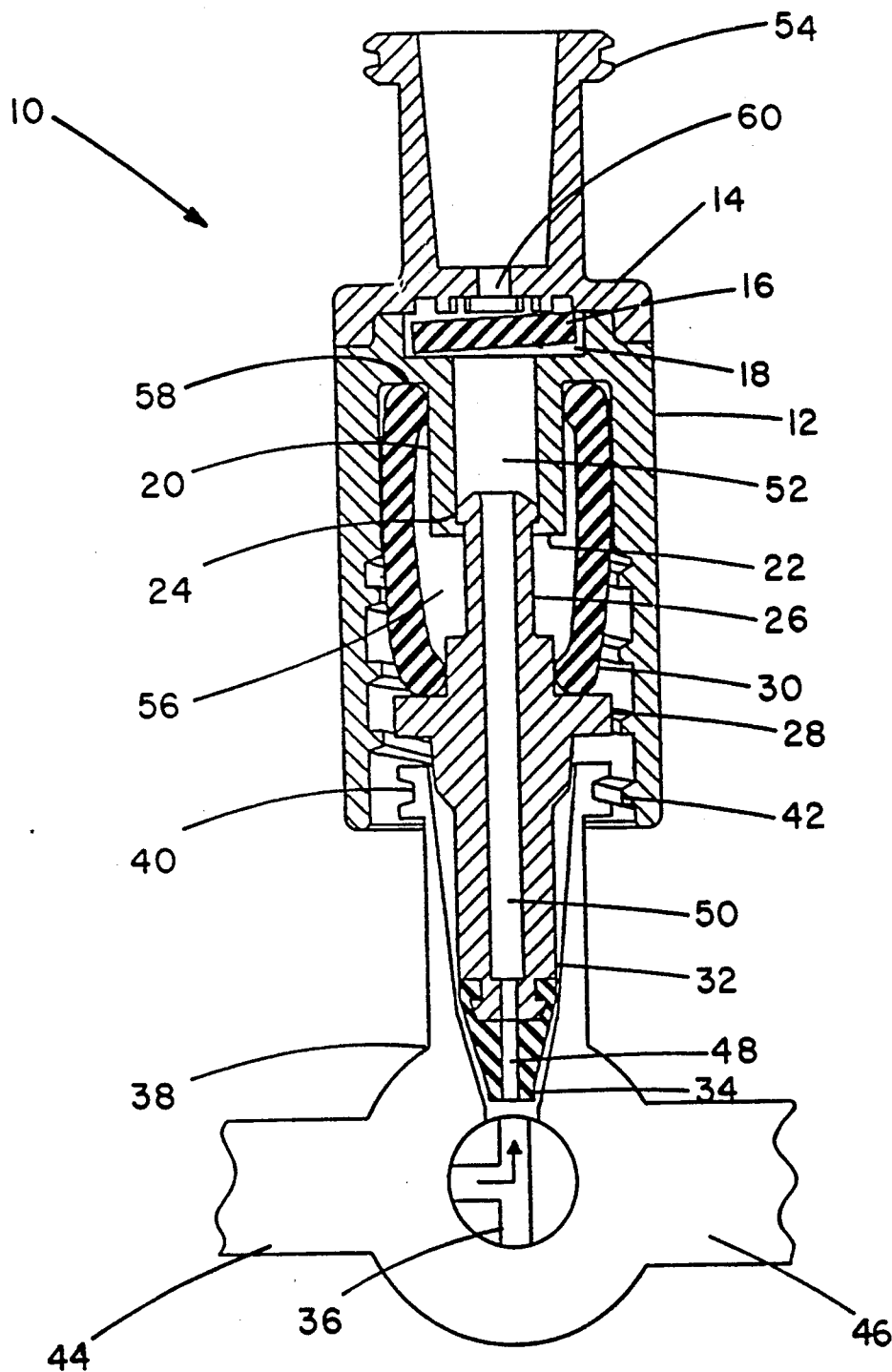
FIG

FLUID SAMPLING METHOD

This application is a continuation-in-part of co-pending U.S. Pat. application Ser. No. 07/694,546 filed May 2, 1991, now U.S. Pat. No. 5,167,238, and which is assigned to the assignee of the present application.

FIELD OF THE INVENTION

This invention relates to methods for sampling fluids, and more particularly for sampling blood flowing in a line with disengagement control.

BACKGROUND OF THE INVENTION

It is known in the art that the number of needle insertions for sampling is desirably minimized; and that valving may be used to facilitate a plurality of samples to be successively taken, with if desired different syringes, from one needle site. It is known that a stopcock can be used here to control flow. It is known too to incorporate a check valve in a blood specimen collection device, to prevent blood backflow into the patient. Use of an elastomerically receding member to create a negative pressure upon the end of dispensing from, for example, a syringe, to prevent undesirable fluid movement after the desired dispensing is known.

SUMMARY OF THE INVENTION

It has been discovered that repeated sampling, as from a single sampling or needle site, can be carried out, with simplicity, economy, freedom from fluid exposure and undue waveform compromise, and cleaning difficulties, if there is provided, with a valve for fluid, a probe to operatively engage the valve, and an actuator, a resilient member deformed by actuator movement to resiliently force the probe into operative engagement with the valve to sealingly engage the probe, and resuming its undeformed configuration upon reverse movement of the actuator, probe tip toward the valve; the probe tip is elastomeric and engages a stopcock valving portion; Luer male threads on a housing-actuator engage female Luer threads on a stopcock to move the probe toward the valve; there is a passage through the probe and housing to a check valve permitting flow only in a direction away from the stopcock; and a fitting with female Luer threads is provided just downstream of the check valve.

PREFERRED EMBODIMENT

Description of the preferred operation follows: drawing, structure, and operation.

DRAWING

There is shown in the drawing a side elevation of the preferred embodiment, partially in section, and partially diagrammatic.

STRUCTURE

The preferred embodiment of a sampling device incorporating the method of the present invention is shown generally at 10.

Housing 12, preferably of injection molded polycarbonate, is solvent-bonded to a female-threaded Luer connector 14, also of injection molded polycarbonate, and carries disk check valve 16 (of 0.040 inch thick Dow Corning Silastic medical grade sheeting) in deeper counterbore 18.

Depending from the counterbore 18 portion of housing 12 is probe engagement portion 20, also of injection molded polycarbonate, with inwardly directed rim 22 which engages rim 24 of probe 26 with the probe 26 in a coaxial telescoping relationship with the probe engagement portion 20.

Probe 26 includes ledge 28, an upper surface of which supports elastomeric barrel 30, and probe tip 32 which receives and carries elastomeric tip 34, selectively engageable with valving portion 36 of stopcock 38, which is connected (by means not shown) to a blood flow line.

Barrel 30 is preferably of compression-molded silicone sold by Lexington Medical, South Hill, S.C., under the designation "Dow 4-2483". It is 0.0400 inches in axial dimension, has an outside diameter of 0.275 inches, and a wall thickness through its main body of 0.040 inches.

The upper portion of stopcock 38 includes female Luer threads 40, which engage male Luer threads 42 within housing 12.

A variable volume passage is defined by coaxially aligned internal bores 48, 50, 52 defined by the elastomeric tip 34, probe tip 32, probe 26 and probe engagement portion 20 and by an internal bore 56 defined by the elastomeric barrel 30. The elastomeric barrel sealingly engages the housing 12 at a sealing surface 58 and the ledge 28 of the probe 26 to seal the variable volume passage 48, 50, 52 and 56 and to bias the probe 26 and probe engagement portion to a relatively larger volume position.

OPERATION

In operation, blood is flowing through stopcock 38 from a single needle site, the stopcock valving portion 36 being rotated so that the two coaxial portions of the valving portion opening are aligned (not shown) with stopcock flow path portions 44 and 46. The threads 42 of the housing 12 are engaged with the threads 40 of the stopcock 38. As the threads 40 and 42 are engaged by rotation of the housing, the elastomeric tip 34 is brought into sealing engagement with the valving portion 36. As the housing 12 is further rotated, the rim 24 of the probe 26 disengages telescopingly from the rim 22 of the probe engagement portion 20, compressing the elastomeric barrel 30 axially, reducing the volume of the variable volume chamber or passage 48, 50, 52 and 56 and urging the elastomeric tip 34 into a firmer sealing relationship with the valving portion 36. Air within the variable volume passage 48, 50, 52 and 56 is released to atmospheric pressure through a passage 60 in the connector 14 by action of the check valve 16. The valving portion 36 is then rotated to the position shown in the figure.

A syringe may then be engaged with the female thread 54 of connector 14, and blood drawn through the passage 48, 50, and 52 of probe tip 32, probe 26, and housing 12, through check valve 16, and through a passage 60 into Luer connector 14.

When housing 12 is rotated the other way, after rotating the stopcock valve portion 36 for inline flow once more, the rim 24 of the probe 26 and the rim 22 of the probe engagement portion 20 return telescopingly to an engaged relationship decompressing barrel element 30 axially. The volume of the variable volume passage 48, 50, 52 and 56 is thus increased. As the volume of the variable volume passage 48, 50, 52 and 56 is increased, a negative (less than atmospheric) pressure is automatically created, sealing the check valve 16 and sucking back any blood contained in the probe tip passage 48.

Alternatively, the method of the present invention may be employed with needle sites not employing stopcocks, such as sampling septa (not shown). In such a case a cannula (not shown) may be the tip 34 and the septum would be provided with Luer threads 40 to engage the Luer threads 42 of the housing 12.

Other embodiments within the claims will occur to those skilled in the art.

What is claimed is:

1. A method for withdrawing a sample of a fluid from a sample site on a fluid container, said method being adapted to reducing the amount of excess fluid at the sample site, said method comprising:
   engaging a sampling device with the sampling site, said sampling device defining a variable volume passage with a relatively larger volume position and a relatively smaller volume position and having a tip at one end of the variable volume passage and a valve at another end of the variable volume passage opposite the one end;
   sealing the tip of the sampling device to the sampling site;
   decreasing the volume of the variable volume passage by moving the variable volume passage to a relatively smaller volume position;
   releasing air from the variable volume passage through the valve;
   withdrawing the sample of fluid from the sample site through the variable volume passage in the sampling device;
   increasing the volume of the variable volume passage by moving the variable volume passage to a relatively larger volume position to create a negative pressure in the variable volume passage;
   closing the valve to prevent entry of air into the variable volume passage through the valve;
   drawing the excess fluid into the variable volume passage by action of the negative pressure; and
   disengaging the sampling device from the sampling site.

2. A method as defined in claim 1 wherein:
   further includes a resilient member to bias the variable volume passage toward the relatively larger volume position; the decreasing step further comprises:
   compressing the resilient member of the sampling device to decrease the volume of the variable volume passage against biasing action of the resilient member; and the increasing step further comprises:
   decompressing the resilient member of the sampling device to increase the volume of the variable volume passage by moving the variable volume passage to the relatively larger volume position by the biasing action of the resilient member.

3. A method as defined in claim 2 wherein:
   the valve is a check valve; and the closing step further comprises:
   closing the check valve by action of the negative pressure to prevent entry of air into the variable volume passage through the check valve.

4. A method as defined in claim 3 wherein:
   the engaging step further comprises:
   threadably connecting the sampling device to the sampling site; and the disengaging step further comprises:
   threadably disconnecting the sampling device from the sampling site.

5. A method as defined in claim 4 wherein:
   the compressing step is performed simultaneously with the engaging step; and
   the resilient member is compressed by the action of threadably connecting the sampling device to the sampling site.

6. A method as defined in claim 4 wherein:
   the decompressing step is performed simultaneously with the disengaging step; and
   the resilient member is decompressed by the action of threadably disconnecting the sampling device from the sampling site.

7. A method as defined in claim 2 wherein:
   the sealing step further comprises:
   urging the tip of the sampling device into contact with the sampling site by biasing action of the resilient member.

8. A method as defined in claim 3 wherein:
   the variable volume passage is defined by a plurality of members each defining a plurality of bores in a coaxial telescoping relationship; the decreasing step further comprises:
   moving at least one of the plurality of members defining a bore telescopingly with respect to at least one other member defining a bore from the relatively larger volume position to the relatively smaller volume position; and the increasing step further comprises:
   moving the one member defining a bore telescopingly with respect to the other member defining a bore from the relatively smaller volume position to the relatively larger volume position.

9. A method as defined in claim 8 wherein:
   the resilient member is an elastomeric barrel;
   said method further comprising:
   sealing the one member defining a bore to the other member defining a bore by compressing the elastomeric barrel against a surface of the one member defining a bore and the surface of the other member defining a bore.

10. A method for withdrawing a sample of a fluid from a sample site on a fluid container, said method being adapted to reducing the amount of excess fluid at the sample site, said method comprising:
    engaging a sampling device with the sampling site, said sampling device defining a variable volume passage having a relatively larger volume position and a relatively smaller volume position and having a tip at one end of the variable volume passage and a check valve at another, opposite, end of the variable volume passage and further having a resilient member for biasing the variable volume passage toward the relatively larger volume position;
    sealing the tip of the sampling device to the sampling site;
    compressing the resilient member of the sampling device;
    decreasing the volume of the variable volume passage by moving the variable volume passage to the relatively smaller volume position against biasing action of the resilient member;
    releasing air from the variable volume passage through the check valve;
    withdrawing the sample of fluid from the sample site through the variable volume passage in the sampling device;

decompressing the resilient member of the sampling device;

increasing the volume of the variable volume passage by moving the variable volume position to the relatively larger volume position by the biasing action of the resilient member to create a negative pressure in the variable volume passage;

closing the check valve by action of the negative pressure to prevent entry of air into the variable volume passage through the check valve;

drawing the excess fluid into the variable volume passage by action of the negative pressure; and disengaging the sampling device from the sampling site.

* * * * *